(12) United States Patent
Sato et al.

(10) Patent No.: US 6,691,576 B1
(45) Date of Patent: Feb. 17, 2004

(54) THICKNESS MEASURING DEVICE FOR CYLINDRICAL TANK BOTTOM PLATE

(75) Inventors: Nobuyoshi Sato, Tokyo (JP); Kazuhiro Nojiri, Tokyo (JP); Tatsuya Fukunaga, Tokyo (JP); Fuminori Kiyota, Kitakyushu (JP); Ryota Kajiki, Kitakyushu (JP); Yuji Nishimura, Kitakyushu (JP)

(73) Assignees: Asahi Engineering Co., Ltd., Osaka (JP); Shin Nippon Nondestructive Inspection Co., Ltd., Fukuoka (JP)

( * ) Notice: Subject to any disclaimer, the term of this patent is extended or adjusted under 35 U.S.C. 154(b) by 94 days.

(21) Appl. No.: 10/048,450

(22) PCT Filed: Jul. 31, 2000

(86) PCT No.: PCT/JP00/05123
§ 371 (c)(1),
(2), (4) Date: Feb. 4, 2002

(87) PCT Pub. No.: WO01/11317
PCT Pub. Date: Feb. 15, 2001

(30) Foreign Application Priority Data

Aug. 4, 1999 (JP) .......................................... 11-221656

(51) Int. Cl.⁷ ............................................. G01N 29/26

(52) U.S. Cl. .............................. 73/601; 73/615; 73/623

(58) Field of Search .................... 73/597, 601, 615, 73/623, 625, 628, 620

(56) References Cited

U.S. PATENT DOCUMENTS

| | | | |
|---|---|---|---|
| 5,062,298 A | * 11/1991 | Falcoff et al. | ................. 73/597 |
| 5,201,225 A | 4/1993 | Takahashi et al. | ............. 73/615 |
| 5,440,929 A | 8/1995 | Huang et al. | ................. 73/628 |

FOREIGN PATENT DOCUMENTS

| | | |
|---|---|---|
| JP | 64-15959 | 1/1989 |
| JP | 2-194355 | 7/1989 |
| JP | 1-129610 | 9/1989 |
| JP | 5-26654 | 2/1993 |
| JP | 6-347250 | 12/1994 |
| JP | 07-128084 | 5/1995 |
| JP | 7-34308 | 6/1995 |
| JP | 7-294498 | 11/1995 |
| JP | 11-19890 | 1/1999 |

OTHER PUBLICATIONS

Patent Abstracts of Japan, Publication No: 06–347250—Date of Publication: Dec. 20, 1994, Application No: 05–134544, Filed: Jun. 4, 1993, Applicant: Asahi Eng Co Ltd, Inventor: Wada Hirofusa, Himaki Tomihisa, and Moriwaki Shinji.

Patent Abstracts of Japan, Laid–open No: 64–15959, Publication Date: Jan. 26, 1989, Filing Date: Jul. 10, 1987, Applicant: Nippon Kurautokurema Ferusuta K.K., Inventor: Hisayoshi Hiraga.

(List continued on next page.)

*Primary Examiner*—John E. Chapman
(74) *Attorney, Agent, or Firm*—Westerman, Hattori, Daniels & Adrian, LLP

(57) ABSTRACT

Plural auxiliary carts 18 and 19 are connected to a measuring cart 11 in the width direction thereof which travels on a tank bottom plate 31 through universal joint mechanisms 26 and 27. Reflection type ultrasonic probes 22, 23 and coating film thickness gauges 24, 25 are provided with the respective auxiliary carts 18 and 19, and also a rotary encoder 32 which measures a traveling distance of the measuring cart 11 is attached to the measuring cart 11. Based on the outputs of the ultrasonic probes 22, 23, the outputs of the coating film thickness gauges 24, 25 and the outputs of the rotary encoder 32, the actual thickness of the tank bottom plate 31, that is obtained by subtracting the thickness of the coating film at a specific position of the tank bottom plate 31 measured by the rotary encoder, is measured and stored, and the thickness of every portion of the tank bottom plate 31 is displayed on a screen.

6 Claims, 8 Drawing Sheets

OTHER PUBLICATIONS

Patent Abstracts of Japan, Publication No: 02–194355, Publication Date: Jul. 31, 1990, Application No: 01–014300, Filing Date: Jan. 24, 1989, Inventor: Kojima Yoshiaki, Hashizume Daizo, Miyawaki Hiroki, Sugimoto Yukiro, and Mitani Yukio.

Abstract Laid–open No:1–129610, Publication Date: Sep. 4, 1989, Application No: 63–20443, Filing Date: Feb. 18, 1988, Applicant: NKN Corp. Electric Power Developement Co., Ltd., Inventor: Kenzo Hondo, Retsu Shiota, Hidetoshi Ohmi, Yuji Matoba, Takumi Morimoto, and Shunji Kaneko.

Abstract, Laid–open No: 07–34308, Publication Date: Jun. 23, 1995, Application No: 05–65303, Filing Date: Dec. 7, 1993, Applicant: Mitsubishi Heavy Industries Co., Ltd., Inventor: Yoshimi Uedo and Hiroaki Kita.

Patent Abstracts of Japan, Publication No: 07–294498, Publication Date:Apr. 28, 1994, Applicant: NKK Corp, Inventor: Iizuka Yukimichi.

* cited by examiner less than 8mm unmeasurable area caused by columns and attachments inside a tank

THICKNESS MEASURING DEVICE FOR CYLINDRICAL TANK BOTTOM PLATE

TECHNICAL FIELD

The present invention relates to a plate thickness measuring apparatus for a bottom plate of a cylindrical tank that measures plate thickness reduction of a bottom plate of a cylindrical tank such as a fuel tank.

BACKGROUND ART

Up to now, in Japan, a plate thickness measurement of a bottom plate of a cylindrical tank by ultrasonic waves has been performed according to the Notification of the Fire and Disaster Management Agency. That is, as for an annular plate within an inside range of 500 mm from an inside face of a side plate, it is performed at intervals of about 100 mm, for example, at fixed points designated in a staggered manner, and as for other portions of the annular plate and a bottom plate therein, it is performed at fixed points specified at intervals of about 1 m. Then, as the result of the plate thickness measurement of the bottom plate at the above fixed points, if a problem arises where a decrement of plate thickness is detected beyond a reference value, plate thickness measurement is further performed for specified positions at intervals of 30 mm, in a range of 300 mm radius with the position as a center by using ultrasonic waves, and hence the plate thickness reduction of the tank bottom near the problem position is known.

However, the following problems that should be solved exist in the conventional plate thickness measurement of the bottom plate of a cylindrical tank.

(1) In the plate thickness measurement of the tank bottom plate using ultrasonic waves, since acoustic velocities in a coating film portion and a steel plate portion differ greatly, if the measurement is performed from an upper surface of the coating film by using a general ultrasonic thickness gauge, a very large measurement error arises in the determination of the thickness of an actual bottom plate, i.e., steel plate thickness. Although a multi-echo type ultrasonic thickness gauge is developed as a countermeasure for this, if there is backside corrosion, it is difficult to correctly determine the state of the steel plate thickness reduction by the corrosion of the tank bottom plate since a multi-echo may not be obtained.

(2) Therefore, on the occasion of measurement of steel plate thickness, a method is adopted in which plate thickness measurement is performed for only the steel plate portion after removing a coating film portion and a recoat is performed after the measurement, however, there is a problem in that an idle period of a tank becomes long due to the measurement and an economical problem that costs of coating film removal and recoat arise in addition to measurement cost.

(3) Furthermore, there is a problem that, if an unusual plate thickness reduction of the steel plate is not detected by the measurement at spaced fixed points, such as unusual plate thickness reduction is ignored even if it actually exists in a portion except the fixed points. It is thus impossible to detect the plate thickness reduction of the steel plate by local corrosion, and hence it is not possible to grasp the plate thickness reduction of the steel plate covering the whole tank bottom plate.

(4) In addition, there is a problem that plate thickness measurement of the tank bottom plate cannot be performed simply and quickly since the measurement is performed at new fixed points, which are given by performing subdivision with a fixed point as a center, if an unusual plate thickness reduction is detected in the fixed point.

The present invention aims to provide a plate thickness measuring apparatus for the bottom plate of a cylindrical tank which can determine plate thickness reduction of a steel plate covering the whole tank bottom plate without removing the coating of the tank bottom plate.

DISCLOSURE OF INVENTION

A plate thickness measuring apparatus for a bottom plate of a cylindrical tank according to the present invention for attaining the above object has: a measuring cart which travels on a tank bottom plate to be measured; auxiliary carts which are arranged in the width direction of the measuring cart and are attached to the measuring cart through universal joint mechanisms; reflection type ultrasonic probes which measure the thickness of the tank bottom plate, and coating film thickness gauges which measure the thickness of a coating film on a surface of the tank bottom plate, both of which are attached in each of the auxiliary carts; a rotary encoder which is attached to the measuring cart and measures the traveling distance of the measuring cart; and an operation and display unit that inputs the outputs of the ultrasonic probes, the outputs of the coating film thickness gauges, and an output of the rotary encoder, measures and stores the actual thickness of the tank bottom plate that is obtained by subtracting the thickness of the coating film at a specific position of the tank bottom plate based on the outputs of the ultrasonic probes and the outputs of the coating film thickness gauges. Furthermore, the apparatus specifies the position by the rotary encoder, displays the relation between the position of the bottom plate and the thickness thereof on a screen and stores it.

In the plate thickness measuring apparatus for the bottom plate of a cylindrical tank according to the present invention, it is desirable that plural reflection type ultrasonic probes are arranged in the width direction of the measuring cart so that the plate thickness measurement can be performed in the whole width direction of the measuring cart, whereby it becomes possible to measure the plate thickness of almost all the portions of the tank bottom plate by making the measuring cart travel on the tank bottom plate. In this case, it is preferable that the auxiliary carts where the ultrasonic probes are mounted are arranged in plural rows in the traveling direction of the measuring cart, and that the auxiliary carts in each row are arranged in a staggered or step-like pattern in a plan view.

In addition, in the plate thickness measuring apparatus for the bottom plate of a cylindrical tank according to the present invention, it is preferable that the reflection type ultrasonic probe is comprised of a double crystal probe having a transmitting element and a receiving element, and that the coating film thickness gauge is comprised of an eddy current type sensor. It is thus possible to measure and evaluate a state of the plate thickness reduction by the local corrosion of the steel plate over the whole tank bottom plate with high precision without removing the coating of the tank bottom plate.

In the plate thickness measuring apparatus for the bottom plate of a cylindrical tank according to the present invention, it is preferable that an operation handle provided in the measuring cart is detachable, and hence, it is possible to measure the thickness of the tank bottom plate with the measuring cart passing under piping provided above the tank bottom plate. Therefore, even if piping which would be obstructive to the measurement is in a tank, it is possible to measure the thickness of the bottom plate by passing thereunder.

BEST MODE FOR CARRYING OUT THE INVENTION

Figure 1:
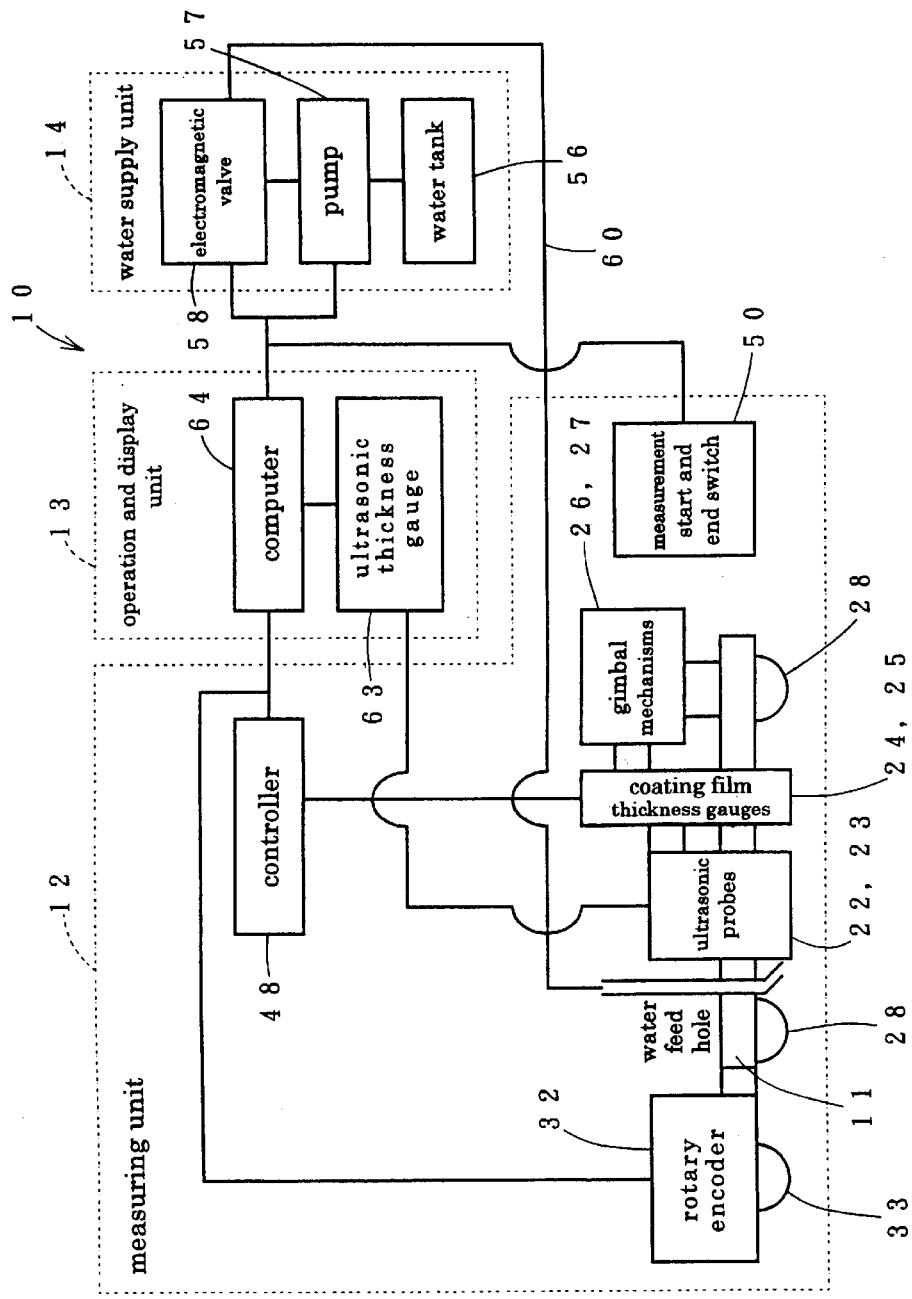
FIG. 1 is a block diagram of each instrument of a plate thickness measuring apparatus for a bottom plate of a cylindrical tank according to an embodiment of the present invention.

As shown in FIGS. 1 to 4, a plate thickness measuring apparatus 10 of a bottom plate of a cylindrical tank according to an embodiment of the present invention has a measuring unit 12 having a measuring cart 11, an operation and display unit 13 which processes measurement data from the measuring unit 12, and a water supply unit 14 which supplies water, which is an example of a coupling medium, to the measuring cart 11. Hereafter, these will be described in detail. The operation and display unit 13 and the water supply unit 14 are not shown in FIGS. 2 to 4.

Figure 2:
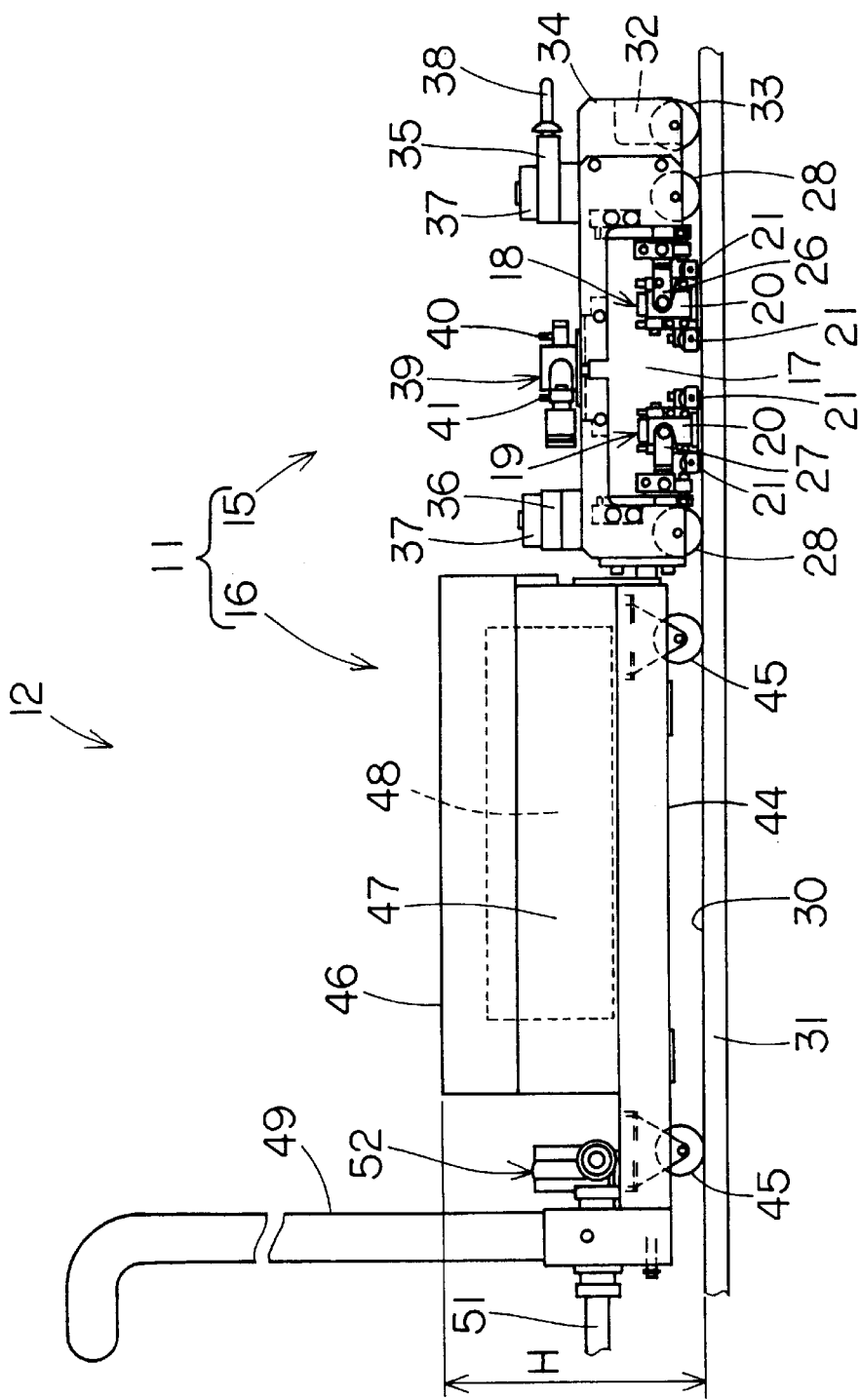
FIG. 2 is a left side view of a measuring unit of the plate thickness measuring apparatus for the bottom plate of the cylindrical tank.
Figure 3:
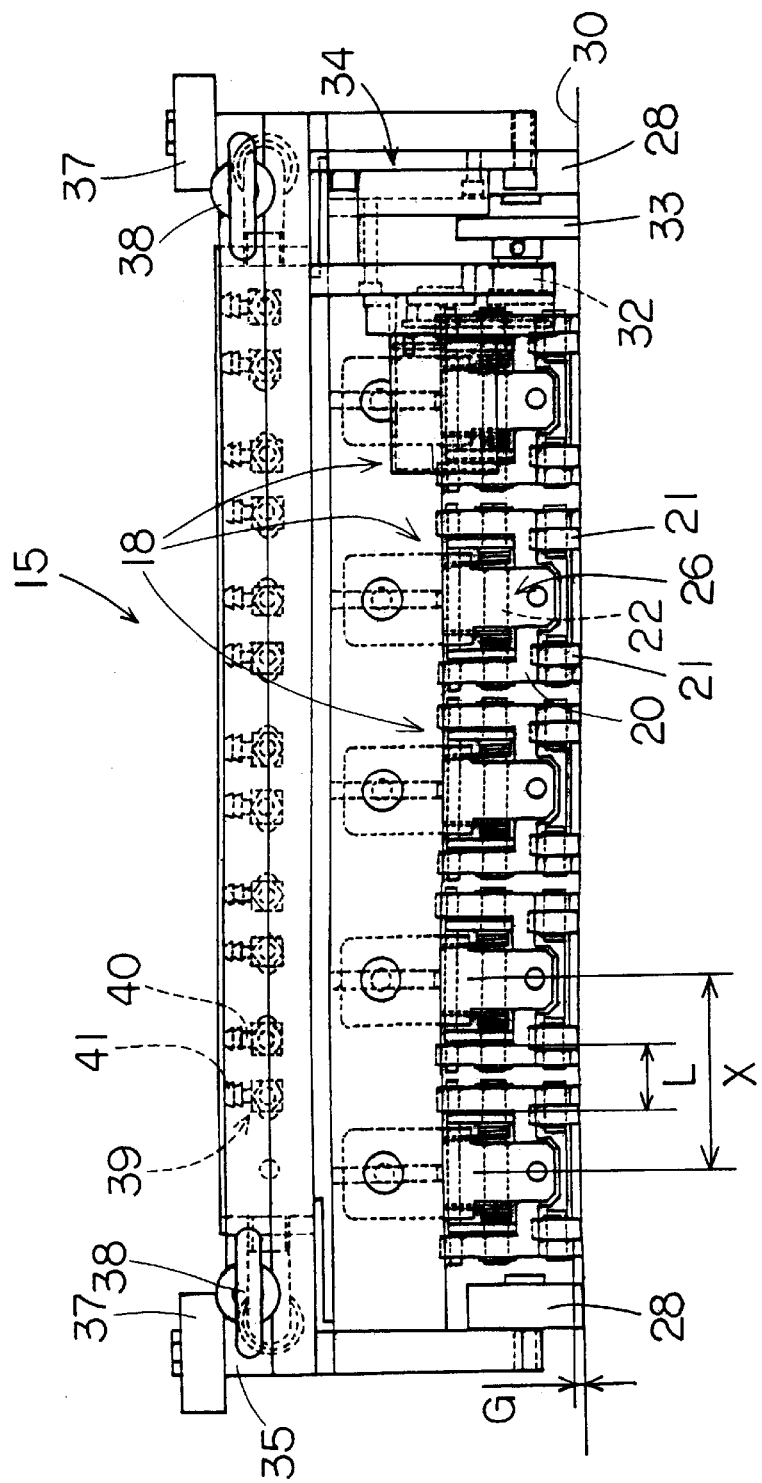
FIG. 3 is a front view of a front measuring cart of the plate thickness measuring apparatus for the bottom plate of the cylindrical tank.
Figure 4:
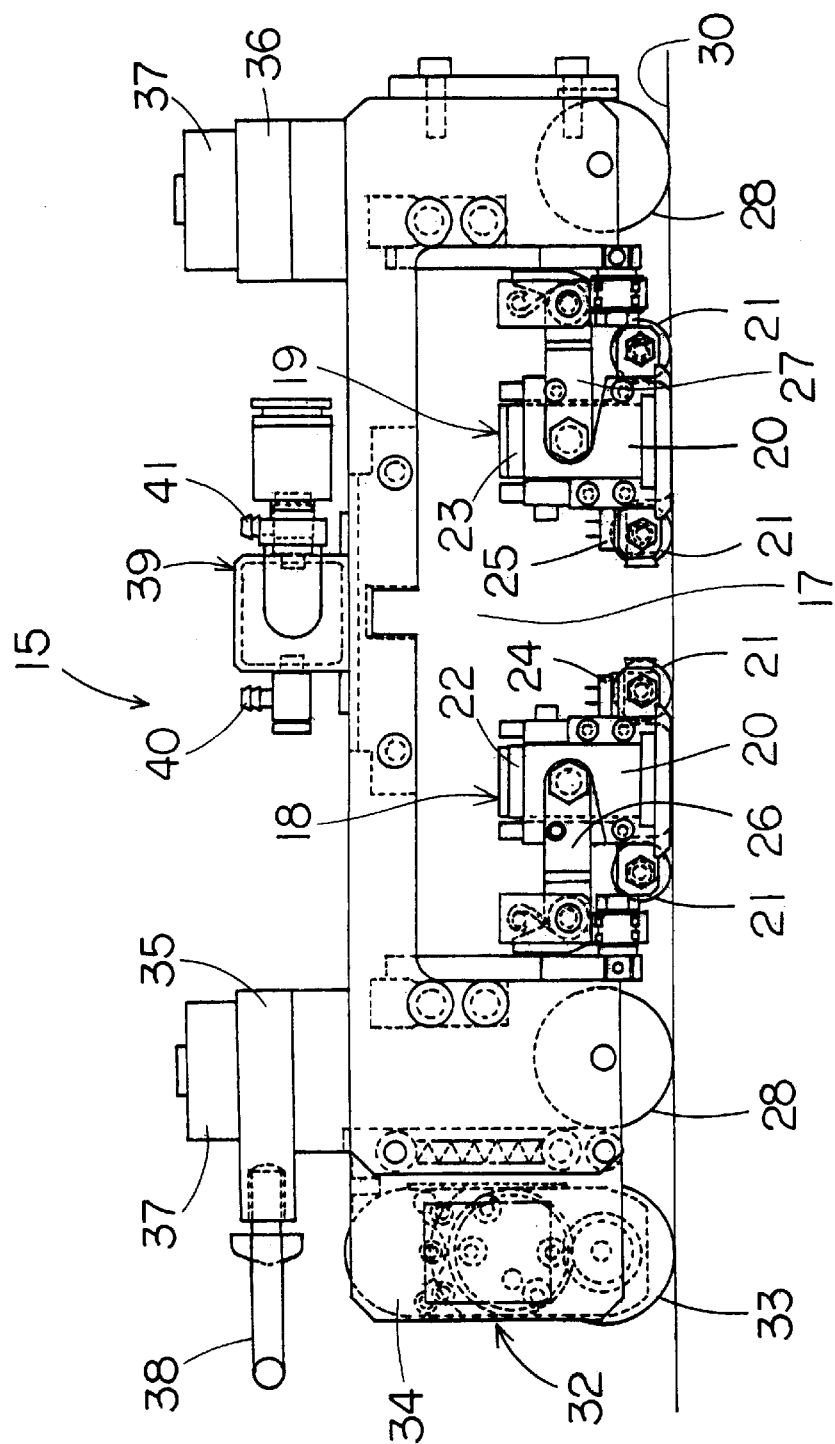
FIG. 4 is a right side view of a front measuring cart of the plate thickness measuring apparatus for the bottom plate of the cylindrical tank.

As shown in FIGS. 1 to 3, the measuring unit 12 is equipped with the measuring cart 11 having a front cart 15 and a back cart 16 that are arranged and connected. Plural auxiliary carts 18 and 19 are provided respectively in the front side and back side of an opening 17 provided in a center of the lower part of the front cart 15. Each of the auxiliary carts 18 and 19 has a frame 20 and free wheels 21 attached in the front, back, right, and left thereof. In a center section of each of the auxiliary carts 18 and 19, as shown in FIG. 4, reflection type ultrasonic probes 22 and 23 are arranged. Coating film thickness gauges 24 and 25 are provided in the back of each auxiliary cart 18, and the front of each auxiliary cart 19, respectively.

Respective auxiliary carts 18 and 19 are attached to the front cart 15 through gimbal mechanisms 26 and 27 each of which is a universal joint mechanism, and auxiliary carts 18 and 19 move with the free wheels 21 of the auxiliary carts 18 and 19 always in contact with a tank bottom surface 30 regardless of shaking of the front cart 15 in a vertical direction. That is, generally, the tank bottom surface 30 does not have a perfect flat surface, but has the undulations, and further, since there are welded portions of joints and corroded portions in the bottom plate 31 locally, there is unevenness on the tank bottom surface 30. Respective auxiliary carts 18 and 19 follow unevenness of the tank bottom surface 30, and the ultrasonic probes 22 and 23 attached to these can move on the tank bottom surface 30 while always having a fixed gap G (refer to FIG. 3). Reference numeral 28 denotes the front, back, right, and left wheels of the front cart 15.

Although the auxiliary carts 18, arranged in the front of the opening 17, and the auxiliary carts 19, arranged in the rear of the opening 17, are arranged in the width direction of the measuring cart 11 at the same intervals respectively, the auxiliary carts 19 in the back row are arranged with shifting by a half pitch (in FIG. 3, X/2) to the auxiliary carts 18 in the front row. The reason why the auxiliary carts 18 in the front row and the auxiliary carts 19 in the back row are arranged in a staggered (zigzag) pattern in such a way is as follows.

Although the ultrasonic probes 22 and 23 have a certain width in flaw detection regions, since each is attached to the auxiliary cart 18 or 19, owing to the presence of the frame 20 and free wheels 21, an approach distance L (refer to FIG. 3) between the ultrasonic probes 22 and 23 adjacent to each other in a row is inevitably limited. For this reason, for example, when using only the ultrasonic probes 22 in the front row (namely, one row), which are arranged in the horizontal single line, in the auxiliary carts 18, belt-like incapable measurement regions arise in interzonal portions with the adjacent ultrasonic probes 22. In order to be able to measure such belt-like incapable measurement regions, produced by the travel of the auxiliary carts 18, by using the ultrasonic probes 23 of the auxiliary carts 19 in the back row (namely, another row), the auxiliary carts 19 are arranged in the central positions between respective auxiliary carts 18 in the moving direction of the front cart 15 so that the ultrasonic probes 23 in the other row can measure the unmeasurable regions of the ultrasonic probes 22 in the one row.

Although an ultrasonic pulse of each of the ultrasonic probes 22 and 23 is emitted from the whole surface of the probe, what can be used effectively in measurement is an ultrasonic wave emitted from a portion the width of which is narrower than this (effective beam width). Therefore, it is necessary to make a pitch X, between centers of each of the auxiliary carts 18 and 19 in the width direction, be in the width of the adjacent ultrasonic probes 18 and 19 not interfering with each other and become twice or less than the effective beam width of each of the auxiliary carts 18 and 19.

Here, if the width of the unmeasurable region of the ultrasonic probes in one row is wide, namely, an unmeasurable region has the width of a half or more of a attachment pitch of each ultrasonic probe, since all regions cannot be measured even by a group of the ultrasonic probes arranged in two rows, the measurement of all the regions in the width direction of the measuring cart 11 becomes possible by providing a step-like group of the ultrasonic probes in three or more rows.

The reflection type ultrasonic probes 22 and 23 used in this embodiment are, for example, split type ultrasonic probes (namely, double crystal probes) each having a transmitting element and a receiving element, which transmit and receive ultrasonic waves through wedges made of acrylic resins, polystyrene resins, or the like. It becomes possible to receive the reflected waves from the lower surface (back face side) of the bottom plate 31 without being influenced by the reflected waves of the ultrasonic waves from the upper surface (namely, the tank bottom surface 30) of the bottom plate 31 of the cylindrical tank near to transmitted pulses. Hence, it becomes possible to accurately measure the distance to a local reduced thickness portion generated in the bottom plate 31.

Eddy current type sensors are used for coating film thickness gauges 24 and 25 provided in the auxiliary carts 18 and 19 respectively. If a coating film is on the surface of the tank bottom surface 30, the plate thickness measured by the ultrasonic probes 22 and 23 becomes the thickness including the total thickness of the coating thickness and steel plate thickness. Then, the actual thickness of the coating film is measured by the coating film thickness gauges 24 and 25 that are comprised of the eddy current type sensors, and a more accurate value is obtained by subtracting it from the distance measurements of the ultrasonic probes 22 and 23.

A rotary encoder 32 is provided in the front of the front cart 15, which detects the rotation speed of the wheels 33 attached to the input shaft of the rotary encoder 32, and the traveling distance of this measuring cart 11 can be electrically measured. A frame 34 to which the rotary encoder 32 is attached is attached to the front cart 15 in a vertically movable or freely movable state, and a wheel 33 of the rotary encoder 32 always rotates in contact with the tank bottom surface 30.

As shown in FIGS. 2 and 4, at the front and back of the upper portion of the front cart 15, a horizontal guide wheel 37 is provided as projecting parts thereof in the right and left sides through supporting tables 35 and 36. When the front cart 15 is located near the inside of the tank side plate, this horizontal guide wheel 37 contacts the inside of the tank side plate, and hence the horizontal guide wheel 37 can smoothly move. Furthermore, the projection length of the horizontal guide wheel 37 can be extended up to 275 mm. In front of the supporting table 35, an eyebolt 38 is provided, and hence it is possible to pull this measuring cart 11 with a rope or the like, one end of which is fixed to the eyebolt 38.

Furthermore, as shown in FIGS. 2 to 4, a water distribution unit 39 is provided in an upper part of the front cart 15, water is supplied to a water spray unit provided in a lower end portion of each of the ultrasonic probes 22 and 23 through water feed holes provided in the front cart 15 via a flexible hose, not shown, which is connected to hose couplers (nipples) 40 and 41, which are arranged before and after, and gaps between the ultrasonic probes 22 and 23, and the tank bottom surface 30 are filled with water. Owing to this, while ultrasonic waves are being sent from the ultrasonic probes 22 and 23 to the bottom plate 31, the reflected waves from the bottom plate 31 can also be sent to the ultrasonic probes 22 and 23.

The back cart 16 connected with this front cart 15 has a cart frame 44 and four wheels 45 provided in the front, rear, right, and left. A housing 47 with a lid 46 is provided on this, and a controller 48 of the eddy current sensors constituting the coating film thickness gauges 24 and 25 is arranged in this housing 47. With this controller 48, the thickness of the coating film applied on the surface of the tank bottom plate 31 is measured, and is outputted to an operation and display unit 13. In addition, although being commonly known, the principle of an eddy current sensor is that the thickness of the coating film is detected by passing an alternating current in a detection coil, detecting that the impedance of the detection coil becomes small if the distance from the upper surface of the bottom plate 31 thereunder becomes large, and comparing this with the reference measured beforehand. In addition, it is also possible to arrange an indicator of the controller 48 on the lid 46 of the housing 47.

At a far back end of the back cart 16, a removable operation handle 49 having the predetermined height (about 60 to 90 cm) is provided, so that an operator can move this measuring cart 11 in back and forth directions with this handle 49. In addition, by removing the handle 49, the whole height of this measuring cart 11 can be reduced, the measuring cart 11 can go under the piping arranged above the tank bottom surface 30, and can test the tank bottom plate 31. Therefore, it is possible to set the height H of the measuring cart 11 to be, for example, about 200 mm when the handle 49 is removed. Furthermore, to reduce it further, it is also possible to set it to be about 100 mm by separating the front cart 15 from the back cart 16.

A cable 51, comprised of bundling signal lines of respective ultrasonic probes 22 and 23, a signal line and a power line for the connection to the controller 48, a signal line of the rotary encoder 32, and control lines of a measurement start and end switch 50, is provided in a back portion of this back cart 16. This cable 51 is fixed to the back cart 16 by a cable stop 52 in the base portion thereof. In addition, the signal of the switch 50 is sent to the operation and display unit 13, and the plate thickness measurement of the tank bottom plate 31 is started and ended.

The water supply unit 14 shown in FIG. 1 has a water tank 56 which can contain sufficient water, a pump 57 which pumps out water from the water tank 56, an electromagnetic valve 58 which turns on and off the water discharged from the pump 57. The start and stop of operation of the pump 57, and ON/OFF of the electromagnetic valve 58 are performed on the basis of instructions of a computer 64 by the signal of the measurement start and end switch 50 provided in the measuring cart 11 being inputted into this computer 64 of the operation and display unit 13. A flexible hose 60 connects this water supply unit 14 with the water distribution unit 39 of the measuring cart 11, and if necessary, water from the water tank 56 is supplied between the ultrasonic probes 22 and 23 and the tank bottom surface 30.

Figure 5:
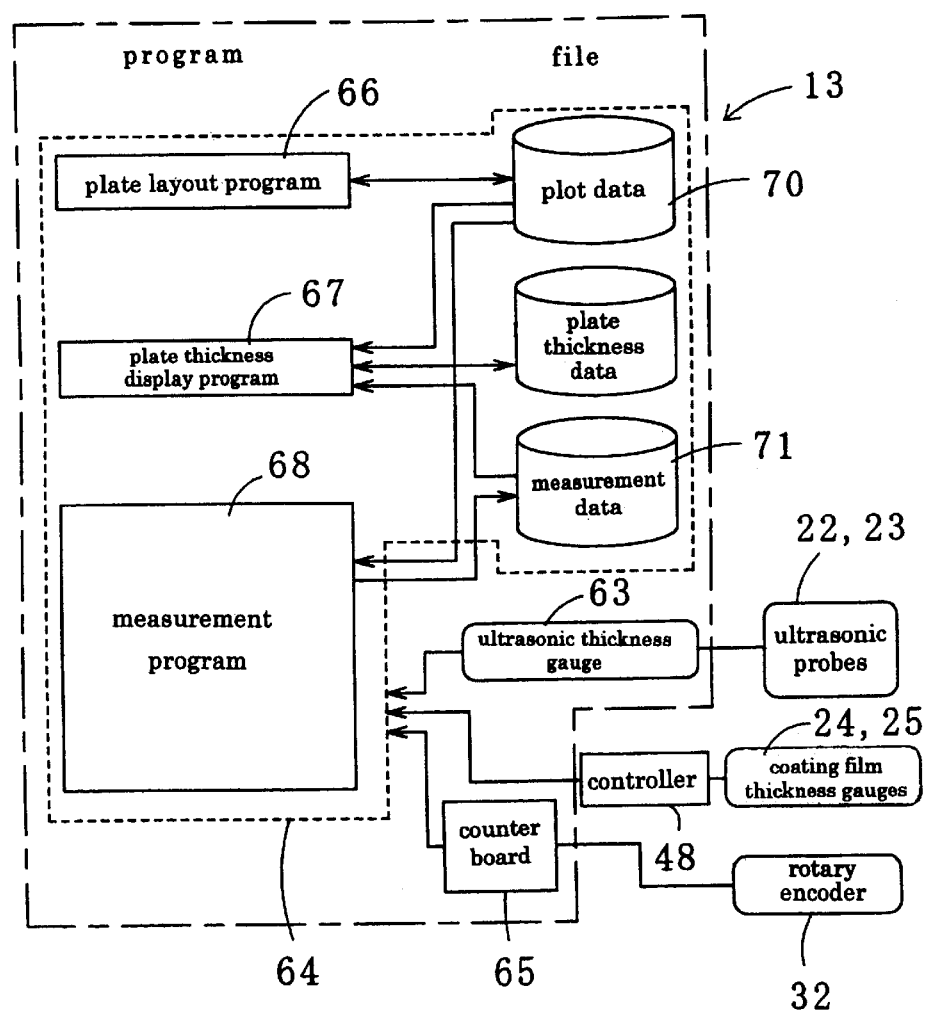
FIG. 5 is a block diagram of a data processing system of a plate thickness measuring apparatus for the bottom plate of the cylindrical tank according to an embodiment of the present invention.

As shown in FIGS. 1 and 5, the operation and display unit 13 has a multi-channel type ultrasonic thickness gauge 63 that sends a predetermined signal to each of the ultrasonic probes 22 and 23 and receives an output signal from each of the ultrasonic probes 22 and 23, and the computer 64 to which this ultrasonic thickness gauge 63 is connected through an I/O plate not shown. This ultrasonic thickness gauge 63, which is a multi-channel type, not only sends pulse signals to the plurality of ultrasonic probes 22 and 23 connected to this, but also measures plate thickness by receiving the pulse signals which the ultrasonic probes 22 and 23 detect, and converts them into a digital signal to send it to the computer 64. The coating film thickness gauges 24 and 25 are connected to the computer 64 through the controller 48, and the rotary encoder 32 is connected through a counter board 65, respectively. The computer 64 is a personal computer that is market-available and comprises a CPU, RAM, ROM, an auxiliary storage device, and I/O devices (for example, an A/D converter), calculates the actual plate thickness of the bottom plate 31 by processing signals sent from the rotary encoder 32, each of the ultrasonic probes 22 and 23, and each of the coating film thickness gauges 24 and 25 by the program which is described below and is set beforehand, and outputs the plate thickness with a position thereof to an attached output device (a display or a printer).

The system outline of this computer 64 is shown in FIG. 5. A plate layout program 66, a plate thickness display program 67, and a measurement program 68, which perform actual processing of the operation and display unit 13, are stored in memory such as a hard disk. Hereafter, these will be described in detail.

Figure 7:
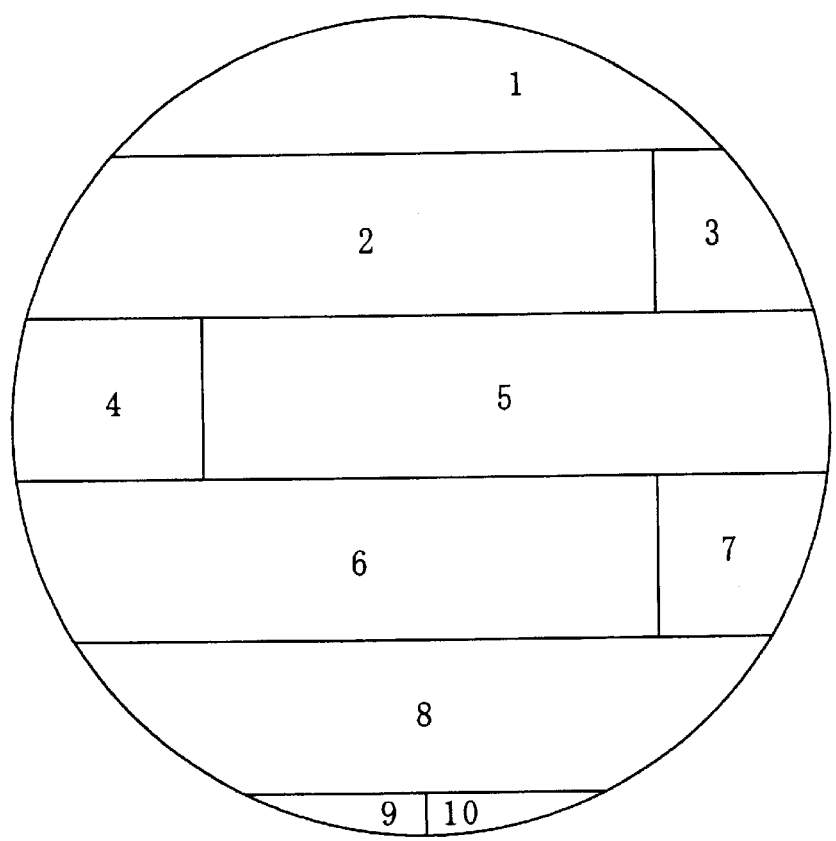
FIG. 7 is a top view showing a plate dividing state of the bottom plate of the cylindrical tank measured by the plate thickness measuring apparatus for the bottom plate of the cylindrical tank.

The above-described plate layout program 66 creates a plate layout plan of the tank bottom plate 31 by inputting basic data, required for the creation of a tank plate cutting diagram, such as the number of the annular plates arranged around the tank bottom plate 31, and the size of a plate which is a unit of the bottom plate 31 (refer to FIG. 7). It becomes possible to calculate the positional information of a plate by making this procedure (namely, a program) stored in a file, and to display only one plate on a CRT etc. independently. Here, the tank plate layout plan created is saved as plot data 70 in a file.

In addition, in the measurement program 68, the positional information in a plate is added to the measured plate thickness data according to the length, measured by the rotary encoder, in the measurement direction by inputting the distance and the measurement direction of the plate (unit plate), which is measured, from an origin by making an arbitrary corner (or a specific position) of the bottom plate 31 be the origin. The data is saved by one point/channel at every fixed distance in the measurement direction, i.e., one data per one subsection. When much data exists in one subsection, a representative value (for example, a minimum plate thickness value) is saved as the data of the subsection. A plate, which is a measuring object, and a corner to be used as an origin are selected by using the plot data 70 created by the plate layout program 66. In consideration of making the measuring cart 11 travel along the periphery of the tank, it is possible to perform plate thickness measurement even in the case of a circular travel of the measuring cart 11 in addition to a straight travel. In addition, a file with the created information on the measuring points, plate thickness, and film thickness is saved as measurement data 71.

Next, the plate thickness display program 67 will be described. The plate thickness display program 67 creates a plate thickness distribution map for every plate and a whole plate thickness distribution map into which these are combined. Although these will be described below, the creation of the plate thickness distribution map per plate will be first described.

Figure 6:
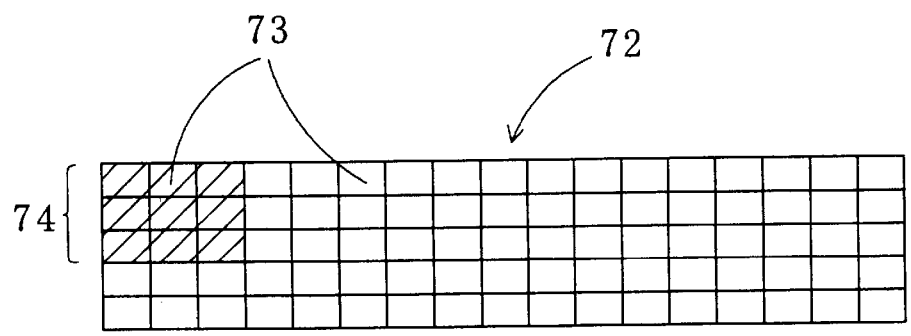
FIG. 6 is a top view of a plate whose thickness is to be measured.

Color-coded display according to the concerned position-plate thickness is performed for every plate by using the plot data 70 and the measurement data 71. The following processing is performed so that a proper representative value of the measurement data 71 may be displayed on one pixel of a CRT (an example of a display) to display it. That is, as shown in FIG. 6, for example, one plate 72 is divided into a lattice a side which is made to be an interval (a fixed interval in the measurement direction) in which the measurement data 71 was acquired, and this one grid is made to be a cell 73. Next, a position and plate thickness are calculated from the measurement data 71, and the plate thickness data is set to the corresponding cell 73. Predetermined operation (for example, acquiring a minimum value) is performed when plate thickness data has been already set to the cell 73 where to be set, and the plate thickness data of the cell 73 is updated. Here, the file generated is saved as per-plate plate thickness data A in a file. Then, pixel size is calculated so that the whole plate may be displayed on the CRT. In addition, this pixel size is made to become an integral multiple of the area of the cell 73. This number of cells gathered is made to be a block 74 (in addition, the block 74 and a pixel have the relation of 1 to 1). A specific example is as follows.

EXAMPLE

When a number of CRT pixels is 640×480, a width of the plate is 7200 mm, and a cell size is 5 mm, 7200/640=11.25≧12 (mm/pixel), which is rounded up, 12/5=2.25≧3 (cells/pixel), which is rounded up, and from the above, 3×3 cells are equivalent to one pixel.

Then, a representative value of the block 74 is calculated by performing a predetermined operation for the cells 73 every block 74 obtained by the above method (for example, a minimum value is acquired), and color-coded display according to the plate thickness is performed to the representative value of this block 74. According to the above procedure, the proper color-coded distribution by the representative value can be displayed.

Next, the creation of a whole plate thickness distribution map will be described.

The color-coded display according to the plate thickness is performed for the whole tank bottom plate 31 by using the per-plate plate thickness data A created with the above-described method. The following processing is performed so that the proper representative value of measurement data may be displayed in one pixel of the CRT for display.

First, the whole tank bottom plate 31 is divided into grids each side of which is the integral multiple (for example, 5 times) of an interval (a fixed interval in the measurement direction) in which measurement data is acquired. This one grid is called a cell H. Then, plate thickness data is set to the concerned cell H from the per-plate plate thickness data A. Predetermined operation (for example, acquiring a minimum value) is performed when plate thickness data has been already set to the cell H to be set, and the plate thickness data of the cell H is updated. Here, a file generated is called whole plate thickness data B.

Next, pixel size is calculated so that the whole tank bottom plate may be displayed on the CRT (it is made to become the integral multiple of the cell H). This number of cells H gathered is called a block D. The block D and a pixel have the relation of 1 to 1, and a specific example is shown below.

EXAMPLE

When the number of CRT pixels is 640×480, the diameter of the tank bottom plate is 48000 mm, and a side of the cell is 25 mm, 48000/480=100 (mm/pixel), which is rounded up, 100/25=4 (cells/pixel), which is rounded up, and from the above, 4×4 cells are equivalent to one pixel.

A representative value of the block D is calculated by performing predetermined operation (for example, acquiring a minimum value) for the cells H every block D obtained by the above method, and color-coded display according to the plate thickness is performed to the representative value of this block D. By these procedures, the proper color-coded distribution according to the representative value can be displayed.

Next, a plate thickness measuring method for the bottom plate 31 of a cylindrical tank where the plate thickness measuring apparatus 10 for the bottom plate of a cylindrical tank according to an embodiment of the present invention is applied will be described.

Since the plate thickness measurement by the ultrasonic probes 22 and 23 is performed by measuring time until a ultrasonic pulse emitted from a transmitting element is sent in order of a coating film, a steel plate, steel plate bottom reflection, the steel plate, and the coating film, and reaches a receiving element, the plate thickness measured by the ultrasonic probes 22 and 23 are a combined thickness containing the total thickness of the coating film thickness and steel plate thickness. On the other hand, the thickness measured by the coating film thickness gauges 24 and 25 is only coating film thickness. Therefore, steel plate thickness, i.e., the thickness of the actual tank bottom plate 31 is obtained by subtracting the coating film thickness, measured by the coating film thickness gauges 24 and 25, from the plate thickness obtained by the ultrasonic probes 22 and 23, respectively without removing the coating of the tank bottom plate 31.

In addition, the ultrasonic probes 22 and 23 and the coating film thickness gauges 24 and 25 which are provided in six sets of auxiliary carts 18 and 19 (one set is hidden in FIG. 3), arranged in the width direction, respectively are attached to the measuring cart 11 under the certain positional relation in a plan view, and hence if what positional relation a certain position in the measuring cart 11 has with the tank bottom plate 31 is known, it is possible to know the positions of the tank bottom plate 31 that positions where the ultrasonic probes 22 and 23 and the coating film thickness gauges 24 and 25 in the auxiliary carts 18 and 19 perform measurement correspond to. Therefore, by attaching the rotary encoder 32, which measures traveling distance, to the measuring cart 11, and grasping the traveling distance from a specific position of the tank bottom plate 31, it is possible to specify in real time the positions of the tank bottom plate 31 that positions where the ultrasonic probes 22 and 23 and the coating film thickness gauges 24 and 25 that are moving perform measurement correspond to, and also to measure the coating film thickness and the plate thickness of the specific position simultaneously. Thus, it is possible to obtain the steel plate thickness at the specific position in the tank bottom plate 31 by combining the plate thickness by the ultrasonic probes 22 and 23, the coating film thickness by the coating film thickness gauges 24 and 25, and the measurement of the rotary encoder 32. In addition, if the relation between a position and steel plate thickness is displayed on a screen, it is possible to determine plate thickness reduction by the corrosion of the steel plate over the whole tank bottom plate 31.

In the actual plate thickness measurement of the tank bottom plate 31, a measuring operator measures by manually moving the measuring cart 11 along a path, determined beforehand, on the tank bottom plate 31. The traveling speed of the measuring cart 1 is determined in consideration of the processing speed of measurement data, and measurement is usually performed at 500 to 1000 mm/second of traveling speed. In addition, in this embodiment, although the measuring cart 11 is made to be a handcart, it is also possible to make the measuring cart 11 be a mobile cart by providing a sensor if necessary, or determining a course beforehand.

Under a structure such as a base heater in a tank which has restrictions in entrance height, by removing the handle 49 provided in the back cart 16, the measuring cart 11 can enter, and it becomes possible to measure the tank bottom plate 31.

In addition, since the controller 48 of the coating film thickness gauges 24 and 25, and the display of measurements are incorporated in the back cart 16, height H is, for example, 200 mm, but it is possible to make the height of the front cart 15 be the height of about 100 mm. For this reason, it becomes possible to measure a gap of up to about 100 mm by performing measurement only by the front cart 15 through separating or offsetting the front cart 15 from the measuring cart 11. At the time of measuring only by the front cart 15, it is possible to adopt a method of attaching a rope to the eyebolt 38 provided in the front end of the front cart 15 and pulling the front cart 15.

If, on the tank bottom plate 31, an unmeasurable region arises near an obstruction such as a wear plate with the obstruction as a center owing to access limitation of the measuring cart 1, it becomes possible to reduce the unmeasurable region by separating or offsetting the front cart 15.

In this embodiment, those that have the effective beam width of 25 mm, and the capacity of being able to detect a flat bottom hole with the diameter of 2 mm which exists in the range of 5 to 35 mm in the measurement direction under a quiescent state are used as the ultrasonic probes 22 and 23, eddy current type sensors which can measure the thickness range of 0 to 2 mm are used as the coating film thickness gauges 24 and 25, and what can perform forward and backward distance measurement in the length measuring precision of 0.1% is used as the rotary encoder 32. In this case, the measurement accuracy of plate thickness at the time of combining the ultrasonic probes 22 and 23 with the eddy current type sensors becomes ±0.1 mm.

Measurement data is recorded in the computer 64 (refer to FIG. 5) as a representative value, for example, in a 5-mm moving interval by finding a minimum value out of all the data read until the moving length becomes 5 mm.

A pulse repetition frequency of the ultrasonic thickness gauge 63 is set to be 500 Hz to 2 kHz, and a range measured at the time of the transmission and reception of ultrasonic pulses from the ultrasonic probes 22 and 23 is made to be a range of 25 mm×3 mm (the value 25 mm is effective beam width that is orthogonal to the moving direction of the ultrasonic probes 22 and 23, and the value 3 mm is effective beam width in the moving direction). Therefore, even if a measuring cart 11 is moved at the rate of 500 to 1000 mm/sec, an incapable flaw detection range in the moving direction does not arise.

Therefore, in the plate thickness measuring apparatus for the bottom plate of a cylindrical tank according to an embodiment of the present invention, measurement will be performed at the following steps as described above. First step (creation of tank bottom plate cutting diagram by plate layout program 66)

Based on the drawing of a tank, a bottom plate cutting diagram is created before the measurement.

Second Step (Measurement by Program 68)

A plate with which measurement is started is selected from the bottom plate cutting diagram.

Third Step (Selection of Origin of Measurement Starting Position)

The origin of a measurement starting position is selected from corners of a plate.

Fourth Step (Input of Measurement Starting Position)

The measurement starting position is inputted in the distance from the origin selected at the third step.

Fifth Step (Selection of Measurement Direction)

The measurement direction is selected from up, down, left, and right directions.

Sixth Step (Selection of Measurement Mode)

A straight line travel or a circular travel is selected.

Seventh Step (Start of Measurement)

The reference point of the measuring cart 11 is aligned with the measurement starting position inputted at the fourth step, and the measurement start switch 50 is pushed. Then, measurement is performed by pushing the measuring cart 11 in the measurement direction selected at the fifth step.

Eighth Step (end of Measurement)

When a measuring cart holder comes to the end point of the plate in the measurement direction, the measurement end switch 50 is pushed.

Ninth Step (Next Measurement)

The measuring cart 11 is moved to a next measurement starting position, and the fourth to eighth steps are repeated. Herewith, the measurement of the plate to be measured is completed.

Tenth Step (Creation of Per-plate Plate Thickness Distribution map)

The color-coded display of the plate to be measured with corresponding to the plate thickness is performed by using the plate thickness display program 67.

Eleventh Step (Measurement of Next Plate)

The measurement of all the plates to be measured is completed by repeating the second to tenth steps.

Twelfth Step (Creation of Whole Plate Thickness Distribution map)

The color-coded display of the whole tank bottom plate corresponding to the plate thickness is performed by using the plate thickness display program 67.

The plate thickness measuring apparatus 10 for the bottom plate of a cylindrical tank according to an embodiment of the present invention applied to the plate thickness measurement of the bottom plate 31 of the cylindrical tank whose inside diameter is 15 m will be further described. The contents of the measurement are divided into initial condition setup, measurement condition setup, a measuring method, and measured result display.

Initial Condition Setup

A tank inside diameter, the number of annular plates, and the size of a basic bottom plate are inputted into the computer 64 of the operation and display unit 13.

Based on an input data, the computer 64 draws an annular plate, and creates bottom plate cutting diagrams by dividing the whole bottom plate vertically or horizontally, and further dividing each of the divided regions. The divided regions are automatically numbered. FIG. 7 shows the bottom plate cutting diagram created when the plate thickness measurement is performed for the bottom plate 31 of a cylindrical tank with an inside diameter of 15 m. Since such processing is described above in detail, it will be omitted here.

Measurement Condition Setup

The number of the plate (refer to FIG. 7), which is measured, is selected from the bottom plate cutting diagram, and the origin, measurement starting point, and measurement direction at the time of measurement are determined about the plate having the selected number.

Measuring Method a) The position of a measurement starting point is inputted in the displacement from the origin.

b) The reference point of the measuring cart 11 is aligned with the measurement starting position, and the measurement start switch 50 is pressed.

c) The measuring cart 11 is moved in the measurement direction at the speed of 500 to 1000 mm/second. The measuring cart 11 is moved so that the traveling direction of the measuring cart 11 may coincide with the optical axis of a laser beam of a laser oscillator installed beforehand so that the measurement direction might be shown.

d) A measurement end switch 50 is pressed when the measuring cart 11 arrives at the end point of the plate.

e) From the end point position, the measuring cart 11 is moved to a next measurement starting position. In addition, when movement is in the direction that is orthogonal (90°) to the measurement direction of the measuring cart 11, a cross-directionally moving cart is used. A cross-directionally moving cart is a dedicated cart for moving the measuring cart 11 in the direction orthogonal to the measurement direction of the measuring cart 11 with the measuring cart 11 being placed thereon.

f) When the measuring cart 11 moves on the whole surface in the plate with the selected number by repeating the above steps a) to e), the measurement of the plate with the selected number is completed.

g) The number of the plate, which is measured next, is selected from the bottom plate cutting diagram, and steps a) to f) are performed.

h) When the plate thickness measurement of all the plates in the bottom plate cutting diagram is completed, it means that the plate thickness measurement of the tank bottom plate 31 is completed.

Measured Result Display

Figure 8:
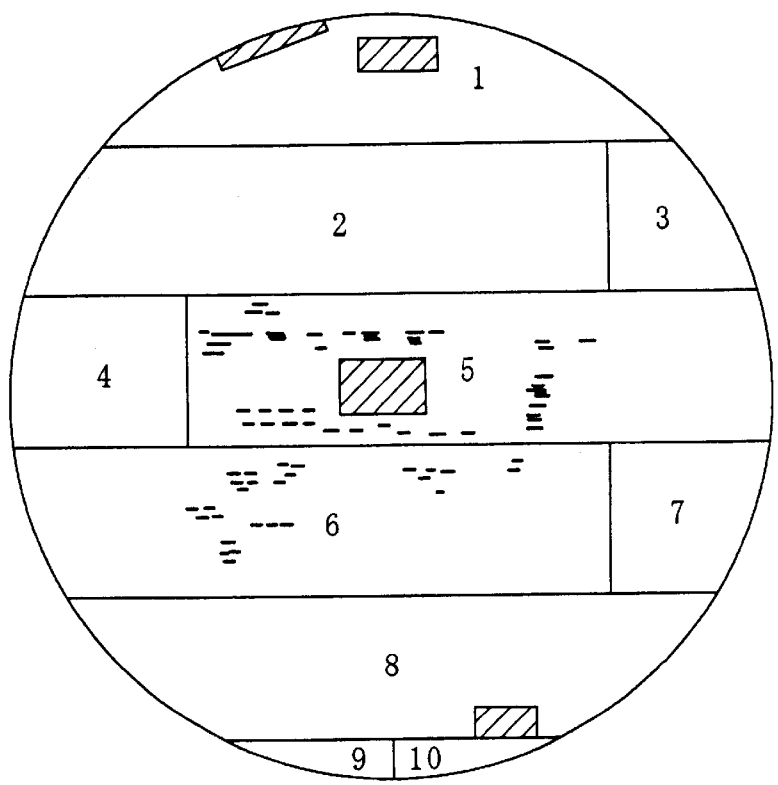
FIG. 8 is an explanatory diagram showing a plate thickness of the bottom plate of the cylindrical tank measured by the plate thickness measuring apparatus for the bottom plate of the cylindrical tank.
Figure 8:
Figure 8:

During the measurement, the measured results of the plate thickness of the bottom plate (steel plate) 31 can be displayed in color-coding according to the grade of plate thickness in real time, and plate thickness reduction can be shown on a screen. After the measurement, the measured results of steel plate thickness can be displayed into the bottom plate cutting diagram in color-coding according to the grade of plate thickness, and the color-coded plate thickness distribution map, a state of plate thickness cross sections in the vertical and horizontal directions at an arbitrary position, or the like can be displayed on a screen by selecting a plate with an arbitrary number. These contents displayed on a screen can be outputted by a color printer that is an example of an output unit. In addition, it is possible to display and output an average of plate thickness, a minimum value of plate thickness, and the distribution of areas of portions, whose plate thickness is more than a fixed plate thickness, according to the number of a plate. The distribution situation of positions with a bottom plate thickness of less than 8 mm against the design bottom plate thickness of 10 mm is shown in FIG. 8 as an example of plate thickness reduction obtained in the plate thickness measurement of the bottom plate 31 of a cylindrical tank with an inside diameter of 15 m. In addition, the relation of the bottom plate thickness and area that is obtained over the whole tank bottom plate 31 is shown in Table 1. Since such processing is described above in detail, it will be omitted here.

TABLE 1

| Class of steel plate thickness (mm) | Area (cm$^2$) | Rate (%) | Note |
|---|---|---|---|
| t ≧ 10 | 845678 | 44.5 | |
| 10 > t ≧ 9.0 | 1031905 | 54.3 | |
| 9.0 > t ≧ 8.0 | 2260 | 0.1 | |
| 8.0 > t ≧ 7.0 | 25 | 0.0 | |
| t < 7.0 | 0 | 0.0 | |
| Not measured | 21080 | 1.1 | Unmeasurable area |
| Total | 1900948 | 100.0 | |

Design steel plate thickness: 10.0 mm
Average steel plate thickness: 9.83 mm
Minimum steel plate thickness: 7.10 mm Moreover, although specific numbers are used for description in the above-described embodiment, the present invention is not limited to these numbers.

Industrial Applicability

In a plate thickness measuring apparatus for the bottom plate of a cylindrical tank according to the present invention, a measuring cart is moved, in which reflection type ultrasonic probes which measure the thickness of a tank bottom plate, coating film thickness gauges which measure coating film thickness on the surface of the bottom plate, and a rotary encoder which measures traveling distance are attached, on the tank bottom plate, to measure the thickness of the actual bottom plate at a specific position of a tank bottom surface, and to display the relation between the position and the thickness in real time on a screen. Hence it becomes possible to accurately, simply, and quickly measure and evaluate plate thickness reduction by the corrosion of a local steel plate over the whole tank bottom plate without removing the coating of the tank bottom plate. Since it becomes possible to perform measurement by setting the traveling speed of a measuring cart to be 500 to 1000 mm/second, it becomes possible to perform high-speed plate thickness measurement.

In a plate thickness measuring apparatus for the bottom plate of a cylindrical tank according to the present invention, if auxiliary carts are arranged in a plurality of rows in the traveling direction of a measuring cart, and furthermore, in a staggered or step-like pattern, it is possible to perform a wide range of plate thickness measurement simultaneously, and to attain easy and rapid measurement.

In addition, in a plate thickness measuring apparatus for the bottom plate of a cylindrical tank according to the present invention, since a double crystal probe of a transmitting element and a receiving element is composed of a reflection type ultrasonic probe, and an eddy current type sensor is composed of a coating film thickness gauge, it is possible to accurately measure and evaluate plate thickness reduction without removing the coating of a tank bottom plate.

In a plate thickness measuring apparatus for the bottom plate of a cylindrical tank according to the present invention, since the height of the whole measuring cart is made to be able to measure the thickness of a tank bottom plate while passing under the piping provided above the tank bottom plate, a large area of the tank bottom plate can be measured.

What is claimed is:

1. A plate thickness measuring apparatus for a bottom plate of a cylindrical tank characterized by comprising:

a measuring cart which travels on a tank bottom plate to be measured;

plural auxiliary carts which are arranged in a width direction of the measuring cart and moreover attached to the measuring cart through universal joint mechanisms;

reflection type ultrasonic probes which measure a thickness of the tank bottom plate, and coating film thickness gauges which measure a thickness of a coating film on a surface of the tank bottom plate, both of which are attached in each of the auxiliary carts;

a rotary encoder which is attached to the measuring cart and measures a traveling distance of the measuring cart; and an operation and display unit which inputs outputs of the respective ultrasonic probes, outputs of the respective coating film thickness gauges and an output of the rotary encoder, measures and stores an actual thickness of the tank bottom plate that is obtained by subtracting the thickness of the coating film at a specific position of the tank bottom plate based on the output of the respective ultrasonic probes and the output of the respective coating film thickness gauges, furthermore, specifies the position by the rotary encoder and displays the relation between the position of the bottom plate and the thickness thereof on a screen by color-coding according to the measured thickness of the tank bottom plate, wherein the respective auxiliary carts are arranged in plural rows in the traveling direction of the measuring cart, and the auxiliary carts are arranged in a staggered or step-like pattern in a plan view, whereby the adjacent ultrasonic probes are prevented from interfering each other and measurement of a whole region of the width direction of the measuring cart is possible by the ultrasonic probes attached to the auxiliary carts, and moreover, the coating film thickness gauges being provided separately from the ultrasonic probes, furthermore, the each ultrasonic probe being comprised of a double crystal probe in which a transmitting element and a receiving element are separated.

2. The plate thickness measuring apparatus for a bottom plate of a cylindrical tank according to claim 1, characterized in that the measuring cart comprises a front cart and a back cart which are arranged and connected front and back, the plural auxiliary carts in two rows arranged front and back are arranged in a staggered pattern in a plan view in an opening formed in a lower middle of the front cart, and furthermore, a horizontal guide wheel is provided respectively in a front and a back of an upper portion of the front cart through a supporting table.

3. The plate thickness measuring apparatus for a bottom plate of a cylindrical tank according to claim 2, characterized in that the ultrasonic probes are provided in a middle portion of the respective auxiliary carts and the coating film thickness gauges are provided in a front portion or a back portion of the respective auxiliary carts.

4. The plate thickness measuring apparatus for a bottom plate of a cylindrical tank according to claim 1, characterized in that an operation handle provided in the measuring cart is detachable, whereby it is possible to measure the thickness of the tank bottom plate by the measuring cart passing under piping provided above the tank bottom plate.

5. The plate thickness measuring apparatus for a bottom plate of a cylindrical tank according to claim 1, characterized in that an ultrasonic thickness gauge is provided such that a pulse repetition frequency added to the respective ultrasonic probes is 500 Hz to 2 kHz.

6. The plate thickness measuring apparatus for a bottom plate of a cylindrical tank according to claim 1, characterized in that an ultrasonic thickness gauge is provided such that a pulse repetition frequency added to the respective ultrasonic probes is smaller than a value which an effective beam width of a traveling direction of the ultrasonic probe is divided by a traveling speed of the measuring cart, whereby plate thickness measurement is possible for all traveling directions of the measuring cart.

* * * * *